United States Patent
Mukthiyar et al.

(10) Patent No.: US 11,891,356 B2
(45) Date of Patent: Feb. 6, 2024

(54) PRODUCTION OF HIGH YIELDS OF LIGHT OLEFINS FROM HEAVY HYDROCARBONS

(71) Applicant: INDIAN OIL CORPORATION LIMITED, Maharashtra (IN)

(72) Inventors: Sadhullah Mukthiyar, Faridabad (IN); Shikha Saluja, Faridabad (IN); Gadari Saidulu, Faridabad (IN); Arumugam Velayutham Karthikeyani, Faridabad (IN); Madhusudan Sau, Faridabad (IN); Debasis Bhattacharyya, Faridabad (IN); Gurpreet Singh Kapur, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 18/112,365

(22) Filed: Feb. 21, 2023

(65) Prior Publication Data

US 2023/0265026 A1    Aug. 24, 2023

(30) Foreign Application Priority Data

Feb. 21, 2022 (IN) .............................. 202221009125

(51) Int. Cl.
*C07C 4/06* (2006.01)
*B01J 29/08* (2006.01)
*B01J 29/40* (2006.01)
*B01J 29/80* (2006.01)

(52) U.S. Cl.
CPC .................. *C07C 4/06* (2013.01); *B01J 29/08* (2013.01); *B01J 29/40* (2013.01); *B01J 29/80* (2013.01); *C07C 2529/08* (2013.01); *C07C 2529/40* (2013.01); *C07C 2529/80* (2013.01)

(58) Field of Classification Search
CPC ... C07C 4/06; C07C 2529/08; C07C 2529/40; C07C 2529/80; B01J 29/08; B01J 29/40; B01J 29/80
See application file for complete search history.

(56) References Cited

U.S. PATENT DOCUMENTS

| | | | |
|---|---|---|---|
| 5,296,131 A | 3/1994 | Raterman | |
| 5,846,402 A | 12/1998 | Mandal et al. | |
| 6,538,169 B1 | 3/2003 | Pittman et al. | |
| 6,656,346 B2 | 12/2003 | Ino et al. | |
| 2018/0264430 A1 | 9/2018 | Sadhullah et al. | |
| 2022/0064551 A1* | 3/2022 | Akah .................... C10G 11/18 |

OTHER PUBLICATIONS

1 European Search Report issued in corresponding application No. EP 23 15 6509, dated Jun. 16, 2023.

* cited by examiner

*Primary Examiner* — Thuan D Dang
(74) *Attorney, Agent, or Firm* — Maschoff Brennan

(57) ABSTRACT

A process for conversion of hydrocarbon feedstock into lighter olefins of $C_2$ to $C_4$ carbons, the process comprising of cracking the hydrocarbon feedstock in a reactor in the presence of a catalyst. The catalyst for short contact time catalytic cracking process of heavy hydrocarbons having contact time less than 1 second to produce light olefins of $C_2$ to $C_4$ carbon in the range of 40 to 60 wt % on fresh feed basis in a fluidized bed reactor which is concentric downflow reactor in presence of catalyst consisting of ultra-stable Y zeolite in the range of 5-10 wt %, 4 to 8 wt % of pentasil zeolite, 2.5-5 wt % of bottom selective material, 0.5-2 wt % of rare earth and 75-88 wt % of support material.

7 Claims, No Drawings

PRODUCTION OF HIGH YIELDS OF LIGHT OLEFINS FROM HEAVY HYDROCARBONS

FIELD OF THE INVENTION

The present invention relates to the process for conversion of hydrocarbon feedstocks into light olefins. More particularly the present invention describes a catalyst with short contact time for conversion of hydrocarbon into high yield of total light olefins of carbon number up to 4 with up to 60 wt % based on fresh feed basis in a concentric down flow reactor.

BACKGROUND OF THE INVENTION

Fluid catalytic cracking (FCC) is one of the most widely used process for the conversion of heavy hydrocarbons into gasoline, light olefins, and other valuable products. The FCC process consists of two major sections namely reactor and regenerator. Hot catalyst particles from the regenerator are contacted with hydrocarbon feedstocks, thereby producing cracked products, and spent coked catalyst.

The coked catalyst is separated from the cracked hydrocarbons products and then stripped using steam to remove residual hydrocarbons. The coked catalyst is then regenerated by burning the coke in presence of air to reactivate the catalyst. The hot catalyst is then recycled to the reactor for making the cracking process continuous.

A variety of process configurations and catalysts have been developed for the FCC process since its invention in 1938. The FCC process has a major advantage of operating flexibility wherein the process can either operate in maximum fuels mode or the maximum chemicals mode. Maximum fuels mode provides maximum yields of diesel and gasoline range products with minimum Liquefied Petroleum Gas (LPG) and Dry gas (Hydrocarbon gases of carbon number up to 2 including hydrogen). In Maximum chemicals mode, products such as LPG and Dry gas are maximized. The maximum fuels and chemicals mode are made possible by altering the operating conditions and catalyst in the FCC system.

Also, as per the market research report from fortune business insights published on September 2021, the global electric vehicle market is anticipated to grow from $287.36 billion in 2021 to $1318.22 billion in 2028 at a CAGR of 24.3% in forecast period. Due to this booming electrical vehicle market, it shall result in reduced consumption of fuels in view of gradual transition towards electric based vehicle from fuel-based vehicles. In view of this refiners need to change the product slate from fuels mode to chemicals mode.

Cat cracking unit in the refineries will play a vital role in changing the product slate from fuels to chemicals. Many high severity cat cracking units have been implemented for increasing the chemicals yield. Reactor configuration also plays an important role operating the cat cracking unit at high severity. The reactor configuration and catalyst system of FCC process has also seen a sea change ever since its invention with model 1 unit in 1942. Riser cracking was invented by shell in 1972 with the intention of reducing the contact time between catalyst and hydrocarbons. However, the product selectivity in the upflow riser configuration was later observed to be limited due to inherent catalyst back mixing. Researchers came out with Downflow reactor configuration to overcome the catalyst back mixing observed in the upflow riser configuration. Various designs in downflow configuration have come up since then, but very few have come up to the commercial scale. The main challenge being faced is to efficiently contact the catalyst and hydrocarbons for realising the benefit of no catalyst back mixing. As the downflow reactor is scaled up, it becomes difficult to distribute the catalyst uniformly. Concentric downflow reactor design ensures uniform distribution of catalyst, and its annular curtain flow ensures proper contact between catalyst and hydrocarbons due to relatively lower radial distance requirement. Catalyst role in such a reactor configuration becomes equally important as the reduced contact time will affect the conversion levels and the light olefins yield. This invention describes about the process and catalyst wherein the light olefins yield as well as its selectivity is maximized without compromising on conversion levels.

U.S. Pat. No. 5,846,402 describes about a process for selective catalytic cracking of a petroleum-based feedstock to produce a product having a high yield of liquefied petroleum gas (LPG) and light olefins having 3 to 4 carbons includes providing a fluidized bed reactor with specified catalyst components in a fluidized bed reactor. The process produces an LPG yield ranging up to 40 to 65 wt % of the fresh petroleum-based feedstock, a selectivity for the light olefins of at least 40 wt % and a selectivity for the LPG of at least 45 wt %

U.S. Pat. No. 6,656,346 describes about a process for converting heavy oil fraction is catalytically cracked by contacting the oil with a catalyst mixture consisting of 60 to 95 wt % of a base cracking catalyst containing an ultra stable Y-type zeolite and less than 0.5 wt % of rare-earth metal oxide, and 5 to 40 wt % of an additive containing a shape-selective zeolite, in a fluid catalytic cracking apparatus under conditions that a reaction zone outlet temperature is in the range of 580 to 630° C., the catalyst/oil ratio is in the range of 15 to 40 wt/wt, and the contact time of hydrocarbons in the reaction zone is in the range of 0.1 to 1.0 seconds to increase light olefins yield.

U.S. Pat. No. 6,538,169 describes an FCC process for obtaining light olefins comprises contacting a hydrocarbon feed stream with blended catalyst comprising regenerated catalyst and coked catalyst. The catalyst has a composition including a first component and a second component. The second component comprises a zeolite with no greater than medium pore size wherein the zeolite comprises at least 1 wt-% of the catalyst composition. The contacting occurs in a riser to crack hydrocarbons in the feed stream and obtain a cracked stream containing hydrocarbon products including light olefins and coked catalyst. The cracked stream is passed out of an end of the riser such that the hydrocarbon feed stream is in contact with the blended catalyst in the riser for less than or equal to 2 seconds on average.

With the future scenario of the refinery products being gradually converted to chemicals, it is important for refiners to address the issue of processing heavy hydrocarbon feedstocks into higher light olefins yield as compared to existing processes. Conventional FCC process utilizes up flow riser configuration wherein the catalyst and hydrocarbon move upwards, and the minimum contact time of 2-2.5 seconds is required to overcome the system hardware operating limitations. Due to relatively high contact time, the undesired products such as coke and dry gas increases, whereas in the downflow system where hydrocarbon feed and catalyst contact and move co-currently downward, there is an improvement in the product selectivity due to the narrow residence time operated in this setup. However, the product conversion also reduces due to the reduced contact time. The product conversion is therefore increased by increasing the reaction temperature. It is also observed that when the temperature is increased the propylene selectivity of LPG increases whereas the ethylene selectivity in dry gas and butylenes selectivity in LPG decreases. But the overall olefins yield increases with temperature parabolically. The present invention describes about—a specific catalyst system in a specified operating range in a concentric downflow reactor to achieve the desired objective.

Objectives of the Present Invention

It is a primary objective of the present invention is to provide a process for maximizing the yields of $C_2$-$C_4$ light olefins.

It is the further objective of the invention to minimize the yield of undesired products such as coke, LCO (Light cycle Oil) and CLO (Clarified Oil). It is the further objective of the invention to recycle the undesired products such as LCO and CLO for generating the required amount of coke for satisfying the heat requirement of the reactor.

It is the further objective of the invention to burn the undesired products such as LCO and CLO in the regenerator for satisfying the heat requirement of the reactor. The products generated such as LCO and CLO can be recycled to the regenerated at one more location so as to maintain the uniform temperature across the regenerator while burning out the liquid products in the regenerator.

It is the further objective of the present invention is to provide a catalyst with short contact time for conversion of hydrocarbon into high yield of total light olefins.

It is a further objective of using a concentric downflow reactor for maximizing the yield of light olefins of $C_2$-$C_4$.

SUMMARY OF THE INVENTION

The present invention relates to a process for conversion of hydrocarbon feedstock into lighter olefins of $C_2$-$C_4$ carbons in the presence of catalyst system comprising of 7-10 wt % of an ultra-stable Y zeolite; 4-8 wt % of shape selective pentasil zeolite; 2.5-5 wt % of bottom selective material; 0.5-2 wt % of rare earth metals; and 75-88 wt % of support material wherein the cracking of feedstock is carried out in the temperature of range of 550 to 650° C., weight hourly space velocity (WHSV) in the range of 100-300 hr-1 and a pressure in the range of 1-4 kg/cm2 g in a reactor which is essentially a concentric downflow reactor and wherein the ratio of catalyst to hydrocarbons is 25-40 wt/wt, and wherein 0 to 50% of the products from the concentric downflow reactor is being recycled and wherein the process yields upto 65 wt % of fresh feed as light olefins of $C_2$-$C_4$ hydrocarbons.

In another embodiment, the coked catalyst is separated from the cracked hydrocarbons at the exit of the concentric downflow reactor through a stripper and is transferred to the regenerator in the presence of an oxygen containing gas and at a temperature ranging from 650° C. to 750° C. to burn off the coke and provide a regenerated catalyst having a coke on catalyst less than 0.1 wt %, wherein coked catalyst is continuously circulated between the regenerator and concentric downflow reactor.

In a preferred embodiment, the residence time of catalyst in the concentric downflow reactor is in the range of 0.1 to 1 seconds.

In a preferred embodiment, products having a boiling range above 200° C. are partly recycled back into the stripper section at one or more locations; and the products having a boiling range above 200° C. are partly recycled back into the regenerator section at one or more locations.

In another embodiment, the cracking of feedstocks carried out in the temperature of 620-640° C. and WHSV of 120-150 hr-1 and a catalyst to hydrocarbon ratio of 35-40.

In yet another embodiment, the catalyst is a catalyst system comprising of 8-9 wt % of an ultra-stable Y zeolite; 6-7 wt % of shape selective pentasil zeolite; 4-5 wt % of bottom selective material; 0.5-1 wt % of rare earth metals; and 80-82 wt % of support material.

DESCRIPTION OF THE INVENTION

The present invention provides a catalyst with short contact time for conversion of heavy hydrocarbon feed to light olefins especially carbon number 2 to 4 in a fluidized bed reactor in presence of a micro spherical catalyst.

In an embodiment of the present invention the heavy hydrocarbon feedstock is converted into high yield of light olefins through a concentric downflow reactor in presence of micro spherical catalyst consisting of a large pore component having silica to alumina ratio at least 10, a medium pore component having silica to alumina ratio at least 30, a non crystalline silica alumina component, phosphate compound, a rare earth compound and a non active support material. The large pore component is essentially the Y zeolite having the pore size between 7 to 10 Å. The medium pore zeolite is essentially the shape selective pentasil zeolite. Cracking the heavy hydrocarbon feedstock in a concentric downflow reactor in presence of multifunctional micro spherical catalyst consisting of ultra stable Y zeolite in the range of 5-10 wt %, 4-8 wt % of shape selective pentasil zeolite, 2.5-5 wt % of active material which is bottom selective material, 0.5-2 wt % of rare-earth, rare-earth materials are essentially Lanthanum and cerium and 75-88 wt % of support material. Bottom selective material is essentially the mesoporous acidic alumina used to pre-crack the heavy hydrocarbons before entering into the y zeolite. Cracking of hydrocarbons is carried out in the temperature range of 550-650° C. and weight hourly space velocity (WHSV) in the range of 100-300 hr-1, the contact time in the concentric downflow reactor being maintained in the range of 0.1-1 second, the catalyst is present in the range of 15-45 wt % of the hydrocarbon feedstock in the reactor, pressure in the range of 1 to 4 kg/cm$^2$ g, steam to hydrocarbon in the ratio of 0.1 to 1.0 wt/wt. The process produces total light olefins yield ($C_2$, $C_3$ and $C_4$ carbon atoms) ranging up to 40 to 65 wt. % of the fresh petroleum-based feedstock. The other gaseous products produced in the process are methane, ethane, propane, butane, and hydrogen. The liquid product produced in the process can be fractionated as per the desired cut range. The catalyst gets deactivated during the cracking step due to deposition of coke.

The separation of coked catalyst is carried out at the end of the cracking step in the reactor. The catalyst is separated from cracked products. The separator to the concentric down flow reactor is able to separate the catalyst and the cracked hydrocarbons in a very short time. Lower part of reactor is used as stripper to strip off the entrapped hydrocarbons from the catalyst using steam. The coked catalyst is then transferred to the regenerator which is positioned at the top through a lift line using air as the transferring medium.

The carbon, hydrogen, sulfur & nitrogen deposits on the catalyst are burnt in the regenerator in presence of oxygen at a temperature of 650-750° C. for regeneration of the catalyst.

The regenerated catalyst is then sent to the concentric downflow reactor for cracking the heavy hydrocarbons into light olefins. As the catalyst used in the process is highly coke selective, the coke yield required for satisfying the heat balance may not be possible. In such cases recycle of CLO and LCO range products can be sent to stripper as coke precursors for generating additional coke. In one of the embodiments, a part of CLO and LCO range products can be recycled to regenerator for burning and generating additional heat so as to supply the heat required by the reactor. The process conditions and catalyst being used in the examples are for illustration purpose only. The present invention can be used for any such feedstocks and shall include any feedstocks like $C_4$, Residue hydrocarbons like reduced crude oil and Vacuum Residue, Hydrotreated Vacuum Gas Oil (HDT-VGO), hydrocracker bottom.

Coke selective catalyst means the catalyst when operated with the same operating conditions and feed results in a lower coke yield. This can be seen in the data generated in Example-3, where the products obtained using the different catalyst system with different reactor configuration is provided. It can be seen that the FCC catalyst provides a coke yield of 6.2 wt %, whereas the catalyst of the present invention provides a coke yield of 4.6 wt %. In actual plant, the use of coke selective catalyst will reduce the delta coke in the system. Delta coke is defined as the coke present on the circulating catalyst. The use of high coke selective catalyst will result in reduced delta coke demanding higher catalyst circulation for a given reaction temperature resulting in higher catalytic conversion and thereby improved product yields. In one of the embodiments, the LCO and CLO generated in the process is recycled in the stripper at multiple locations so as to maximize its conversion and coke yield.

Example-1 provides the data for Conventional FCC process utilizes up flow riser configuration where the contact time of in the catalyst and hydrocarbon move upwards, is in the range of 2-2.5 seconds. Due to relatively high contact time, the undesired products such as coke and dry gas increases, it is also observed that when the temperature is increased the propylene selectivity of LPG increases whereas the ethylene selectivity in dry gas and butylenes selectivity in LPG decreases. But the overall olefins yield increases with temperature parabolically. In Example-2 the data generated for the downflow system where hydrocarbon feed and catalyst contact and move co-currently downward with a contact time of catalyst and hydrocarbon in the range of 0.5-1 second, there is an improvement in the product selectivity due to the narrow residence time operated in this setup. However, the product conversion also reduces due to the reduced contact time. The disadvantage of the present step has been overcome by using the catalyst of present invention. In the present invention in Example-3, the product conversion is increased by increasing the reaction temperature with the new catalyst system for improving the yields of light olefins using a concentric downflow reactor with contact time of catalyst and hydrocarbon in the range of 0.5-1 second. The data generated indicates higher Light Olefins ($C_2$-$C_4$) as compared to the other system, lower coke yield and higher propylene selectivity in LPG.

Feed properties of the feedstocks used in this invention have been tabulated in the table 1 below:

| Feed Description | UOM | Hydrotreated VGO | Hydrocracker Bottom |
|---|---|---|---|
| Density @ 15° C. | kg/m³ | 899.1 | 843 |
| CCR | wt % | 0.05 | 0.08 |

-continued

| Feed Description | UOM | Hydrotreated VGO | Hydrocracker Bottom |
|---|---|---|---|
| Sulphur | wt % | 0.04 | 0.007 |
| $H_2$ content | wt % | 13.4 | 14.8 |

Catalyst Components Used in the Present Invention

| Catalyst Components | UOM | CAT-A |
|---|---|---|
| Large pore component | wt % | 10.1 |
| Medium pore component | wt % | 6.2 |
| Non Crystalline component | wt % | 1.75 |
| Phosphate | w % | 5.9 |
| Rare earths | wt % | 0.2 |
| Non active support Material | wt % | 75.9 |

Example-1

Effect of Temperature on Product Yields/Light Olefins Selectivity with Temperature in Riser Reactor Feedstock used: Hydrotreated VGO Catalyst: FCC catalyst with 10 wt % of pentasil zeolite Catalyst loading into the reactor: 8 gms Simulated Contact Time: 2.5 seconds

| Exp Ref No | # | 1739 | 1732 | 1735 | 1743 |
|---|---|---|---|---|---|
| Temperature | ° C. | 550 | 600 | 620 | 650 |
| Fuel gas | wt % | 2.1 | 5.6 | 8.1 | 12.9 |
| LPG | wt % | 35.1 | 39.2 | 37.3 | 32.8 |
| Coke | wt % | 3.1 | 5.2 | 6.2 | 9.0 |
| Ethylene | wt % | 2.8 | 6.0 | 7.0 | 9.7 |
| Propylene | wt % | 14.0 | 17.5 | 18.11 | 17.4 |
| Butylenes | wt % | 9.2 | 10.2 | 10.8 | 8.9 |

Example-2

Concentric downflow reactor Vs Riser Reactor

Feedstock used: HDT VGO

Catalyst: FCC catalyst with 10 wt % of pentasil zeolite

| Exp Ref No Reactor Configuration | # | 1735 Riser | 1709 Concentric Downflow Reactor |
|---|---|---|---|
| Simulated Contact time | Sec | 2.5 | 0.7 |
| Temperature | ° C. | 620 | 620 |
| Fuel gas | wt % | 8.1 | 6.9 |
| LPG | wt % | 37.3 | 36.8 |
| Coke | wt % | 6.2 | 5.9 |
| Ethylene | wt % | 7.0 | 6.6 |
| Propylene | wt % | 18.1 | 18.1 |
| Butylenes | wt % | 10.8 | 10.9 |
| Propylene selectivity in LPG | wt % | 48.6 | 49.1 |
| Total Light Olefins ($C_2$ + $C_3$ + $C_4$) | wt % | 36.0 | 35.6 |

Example-3

Effect of Catalyst and Reactor Configuration
Feedstock used: Hydrotreated VGO

| Reactor Configuration | | Riser | Concentric Downflow | Concentric Downflow |
|---|---|---|---|---|
| Catalyst | | FCC Catalyst | FCC Catalyst | CAT-A |
| Simulated Contact Time | Se | 2.5 | 0.7 | 0.7 |
| Exp Ref No | # | 1735 | 1709 | 1781 |
| Temperature | °C. | 620 | 620 | 620 |
| Fuel gas | wt % | 8.1 | 6.9 | 6.7 |
| LPG | wt % | 37.3 | 36.8 | 38.7 |
| Coke | wt % | 6.2 | 5.9 | 4.6 |
| Ethylene | wt % | 7.0 | 6.6 | 11.2 |
| Propylene | wt % | 18.1 | 18.1 | 22.2 |
| Butylenes | wt % | 10.8 | 10.9 | 10.8 |
| Propylene selectivity in LPG | wt % | 48.6 | 49.1 | 57.2 |
| Total Light Olefins ($C_2 + C_3 + C_4$) | wt % | 36.0 | 35.6 | 44.2 |

Example-4

Effect of High Activity Catalyst with Different Feedstocks in Concentric Downflow Reactor Catalyst: CAT-A

| Feedstocks | | Hydrotreated VGO | Hydrocracker Bottoms |
|---|---|---|---|
| Catalyst | | CAT-A | CAT-A |
| Exp Ref No | # | 1781 | 916 |
| Temperature | °C. | 620 | 620 |
| Fuel gas | wt % | 6.7 | 15.9 |
| LPG | wt % | 38.7 | 56.4 |
| Coke | wt % | 4.6 | 0.9 |
| Ethylene | wt % | 11.2 | 11.2 |
| Propylene | wt % | 22.2 | 30.7 |
| Butylenes | wt % | 10.8 | 19.5 |
| Propylene selectivity in LPG | wt % | 57.2 | 54.51 |
| Total Light Olefins ($C_2 + C_3 + C_4$) | wt % | 44.2 | 61.4 |

Advantages of the Invention

The following are the technical advantages of the present invention over the prior arts 1. High yields of total light olefins.
2. High light olefins selectivity.

We claim:

1. A process for conversion of hydrocarbon feedstock into light olefins of $C_2$-$C_4$ carbons in the presence of a catalyst system, the process comprising:
    cracking of the hydrocarbon feedstock in a temperature of range of 550° C. to 650° C., weight hourly space velocity (WHSV) in a range of 100-300 hr$^{-1}$ and a pressure in a range of 1-4 kg/cm$^2$ g in a concentric downflow reactor,
    wherein the catalyst system comprises 7-10 wt % of an ultra-stable Y zeolite; 4-8 wt % of a shape selective pentasil zeolite; 2.5-5 wt % of a bottom selective material, wherein the bottom selective material is mesoporous acidic alumina; 0.5-2 wt % of rare earth metals; and 75-88 wt % of a support material,
    wherein the hydrocarbon feedstock comprises feedstock selected from the group consisting of $C_4$, reduced crude oil, Vacuum Residue, Hydrotreated Vacuum Gas Oil (HDT-VGO) and hydrocracker bottom,
    wherein the catalyst is present in the range 25-40 wt. % of the hydrocarbon feedstock, and
    recycling 0 to 50% of products from the concentric downflow reactor
    to yield 40-65 wt % of fresh hydrocarbon feedstock as light olefins of $C_2$-$C_4$ carbons.

2. The process as claimed in claim 1, further comprising separating coked catalyst from the cracked hydrocarbons at the exit of the concentric downflow reactor through a stripper, transferring the coked catalyst to a regenerator in the presence of an oxygen containing gas and at a temperature ranging from 650° C. to 750° C. to burn off the coke, and providing a regenerated catalyst having a coke on catalyst less than 0.1 wt %, wherein the coked catalyst is continuously circulated between the regenerator and concentric downflow reactor.

3. The process as claimed in claim 2, wherein the catalyst has a residence time in a range of 0.1 to 1 seconds in the concentric downflow reactor.

4. The process as claimed in claim 2, further comprising partly recycling back the products having a boiling range above 200° C. into a stripper section at one or more locations.

5. The process as claimed in claim 1, further comprising partly recycling back products having a boiling range above 200° C. into a regenerator section at one or more locations.

6. The process as claimed in claim 1, wherein the cracking of the hydrocarbon feedstock is carried out in a temperature of range of 620-640° C. and WHSV of 120-150 hr$^{-1}$, and a catalyst to hydrocarbon ratio of 35-40 wt/wt.

7. The process as claimed in claim 1, wherein the catalyst system comprises 8-9 wt % of an ultra-stable Y zeolite; 6-7 wt % of shape selective pentasil zeolite; 4-5 wt % of bottom selective material, wherein the bottom selective material is mesoporous acidic alumina; 0.5-1 wt % of rare earth metals; and 80-82 wt % of support material.

\* \* \* \* \*